(12) United States Patent
Chiu et al.

(10) Patent No.: US 10,099,048 B2
(45) Date of Patent: Oct. 16, 2018

(54) DEVICE PORT CLEANER

(71) Applicant: Turnstone Technologies, LLC, Carson City, NV (US)

(72) Inventors: Aaron Chiu, El Paso, TX (US); Cesar Aguilera, Ciudad Juarez (MX); Enrique Delgado Macias, Ciudad Juarez (MX)

(73) Assignee: Turnstone Technologies, LLC, Carson City, NV (US)

( * ) Notice: Subject to any disclaimer, the term of this patent is extended or adjusted under 35 U.S.C. 154(b) by 0 days.

(21) Appl. No.: 15/582,547

(22) Filed: Apr. 28, 2017

(65) Prior Publication Data

US 2018/0256879 A1  Sep. 13, 2018

Related U.S. Application Data

(60) Provisional application No. 62/470,016, filed on Mar. 10, 2017.

(51) Int. Cl.
*B43K 5/14* (2006.01)
*A61M 39/16* (2006.01)
*B08B 9/023* (2006.01)
*A61M 39/10* (2006.01)
*A61M 39/20* (2006.01)

(52) U.S. Cl.
CPC .......... *A61M 39/162* (2013.01); *A61M 39/10* (2013.01); *A61M 39/20* (2013.01); *B08B 9/023* (2013.01); *A61M 2039/1033* (2013.01)

(58) Field of Classification Search
CPC .... A61M 39/162; A61M 39/20; A61M 39/10; A61M 2039/1033
See application file for complete search history.

(56) References Cited

U.S. PATENT DOCUMENTS

| | | | |
|---|---|---|---|
| 5,554,135 A * | 9/1996 | Menyhay | A61M 39/162 138/89 |
| 6,419,825 B1 | 7/2002 | Hahmann et al. | |
| 7,780,794 B2 * | 8/2010 | Rogers | A61B 19/34 134/6 |
| 7,985,302 B2 | 7/2011 | Rogers et al. | |
| 8,065,773 B2 * | 11/2011 | Vaillancourt | A61L 2/235 15/104.93 |
| 8,172,825 B2 | 5/2012 | Solomon et al. | |
| 8,206,514 B2 | 6/2012 | Rogers et al. | |
| 8,336,152 B2 * | 12/2012 | Vaillancourt | A61B 1/122 15/104.93 |
| 8,388,894 B2 * | 3/2013 | Colantonio | A61L 2/18 422/119 |
| 9,192,443 B2 * | 11/2015 | Tennican | A61B 19/0256 |
| 9,750,929 B2 * | 9/2017 | Ma | A61M 39/162 |
| 2006/0030827 A1 | 2/2006 | Raulerson et al. | |
| 2011/0030726 A1 | 2/2011 | Vaillancourt et al. | |
| 2011/0314619 A1 | 12/2011 | Schweikert | |

(Continued)

FOREIGN PATENT DOCUMENTS

CN 103285413 A 9/2013

*Primary Examiner* — Jennifer C Chiang
(74) *Attorney, Agent, or Firm* — CARR Law Firm PLLC

(57) ABSTRACT

A device port cleaner and method of use is provided for cleaning a device port connector, particularly a device port connector for a medical device. The device port cleaner may be connected to the device port connector to clean and/or disinfect the device port connector.

32 Claims, 19 Drawing Sheets

(56) References Cited

U.S. PATENT DOCUMENTS

2012/0111368 A1* 5/2012 Rahimy .............. A61M 39/162
                                                134/22.1
2013/0323117 A1   12/2013 Ma et al.
2015/0273199 A1   10/2015 Adams et al.

* cited by examiner

DEVICE PORT CLEANER

CROSS-REFERENCE TO RELATED APPLICATIONS

This application relates to, and claims the benefit of the filing date of, U.S. provisional patent application Ser. No. 62/470,016 entitled DEVICE PORT CLEANER, filed Mar. 10, 2017, the entire contents of which are incorporated herein by reference for all purposes.

BACKGROUND OF THE INVENTION

Field of the Invention

The present invention relates to device port cleaner, and more particularly to an apparatus and a method for cleaning and/or decontaminating device port connectors, including medical device port connectors.

Description of the Related Art

When treating patients in the medical field, there is a need to prevent the transmission of pathogens into or onto a patient from a potentially contaminated surface of a medical implement, or "site" when infusing fluids or aspiration of fluids to or from a patient. Such pathogens include microorganisms such as bacteria and viruses. The transmission of pathogens into a patient may result in an infection that could be life threatening. Contamination by microorganisms may occur via extrinsic or intrinsic contamination. Extrinsic contamination may occur when preparing or administering medications via vascular access systems. Intrinsic contamination may occur during the manufacturing of the device or medication. Extrinsic contamination may be derived from many possible sources including entry points in the administration sets as well as intravenous line connections between different intravenous sets. Other sources for contamination may include during compound medication preparation, improper use of equipment, improper temperature control, improper sterilization/preparation techniques, or methods.

An important aspect in preventing infections as related to connectors includes the constant change of dressings and careful attention to maintaining hygienic and aseptic access to the connector. Traditionally, cleaning a potentially contaminated surface includes a protocol of alcohol swabbing prior to making the necessary connections to the site. However, a poorly swabbed site can carry microorganisms that, if allowed to enter a patient's body, can cause serious harm. Sometimes, much of medical implements used may be so small that it may be difficult to properly cleanse all portions of the implement, particularly the connecting portions of medical device ports. Even more difficult is the ability to clean the interior surface of device ports that are difficult to access.

SUMMARY

Provided is a device port cleaner, and method of use, for cleaning a device port connector that may be inserted into the device port cleaner.

BRIEF DESCRIPTION OF THE DRAWINGS

For a more complete understanding of the features and advantages thereof, reference is now made to the following Detailed Description taken in conjunction with the accompanying drawings, in which.

DETAILED DESCRIPTION OF THE INVENTION

In the following discussion, numerous specific details are set forth to provide a thorough understanding of the present invention. However, those skilled in the art will appreciate that the present invention may be practiced without such specific details. In other instances, certain specific details, and the like have been omitted inasmuch as such details are not considered necessary to obtain a complete understanding of the present invention, and are considered to be within the understanding of persons of ordinary skill in the relevant art.

In FIGS. 1-20, a device port cleaner 100 for cleaning various device port connectors is shown. In an embodiment, the device port cleaner 100 may be coupled to a device port connector to coat and clean the device port connector with a disinfecting or cleaning agent. The device port cleaner 100 may shield and prevent pathogens, microorganisms, viruses, bacteria, fungus, mold, and other communicable diseases from contacting the surface and septum of the device port connector. The device port cleaner 100 may be used to clean various device ports including but not limited to medical device ports, needle ports, needleless ports, luer locks, catheter hubs, and the like. The device port cleaner 100 may also be used with medical device ports or infusion ports as a prophylactic against pathogens to provide protection for extended time periods.

Figure 1:
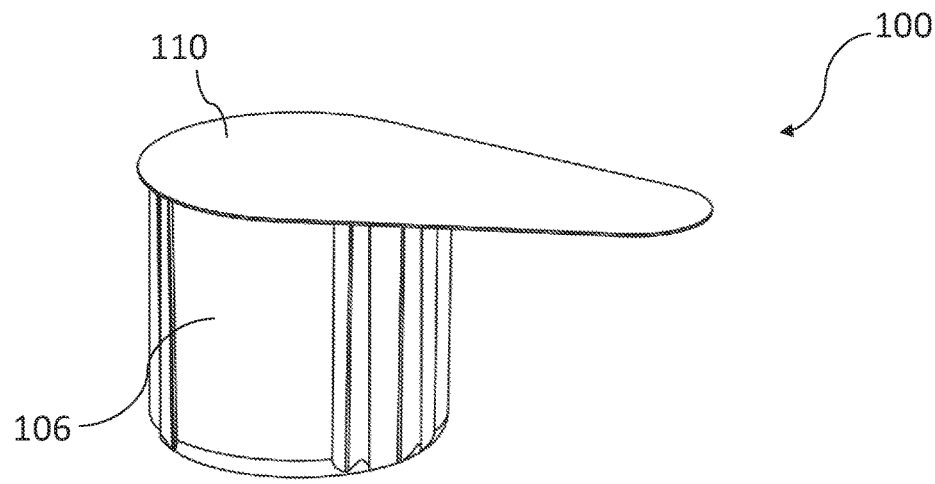
FIG. 1 illustrates an embodiment of a device port cleaner.
Figure 2:
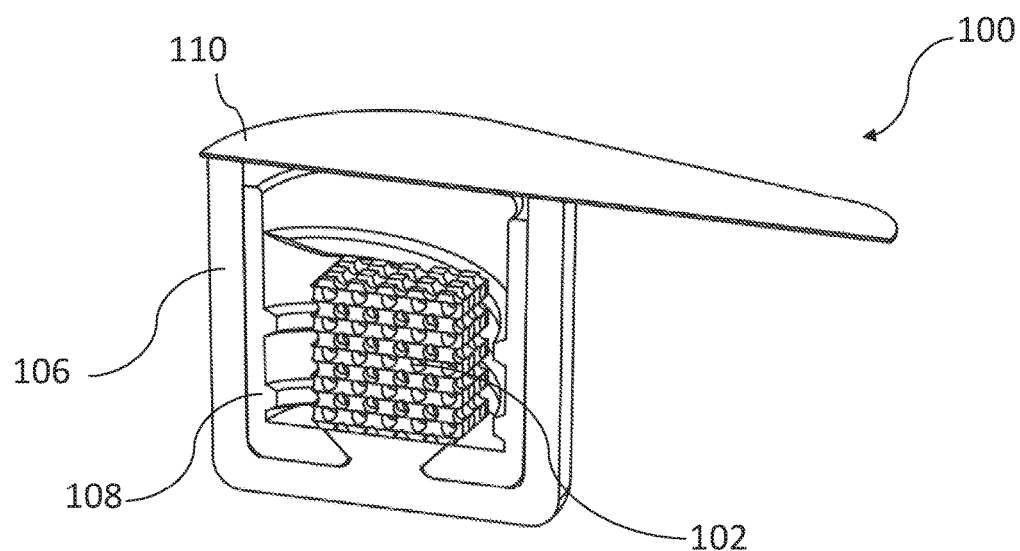
FIG. 2 illustrates a sectional view of the device port cleaner.
Figure 3:
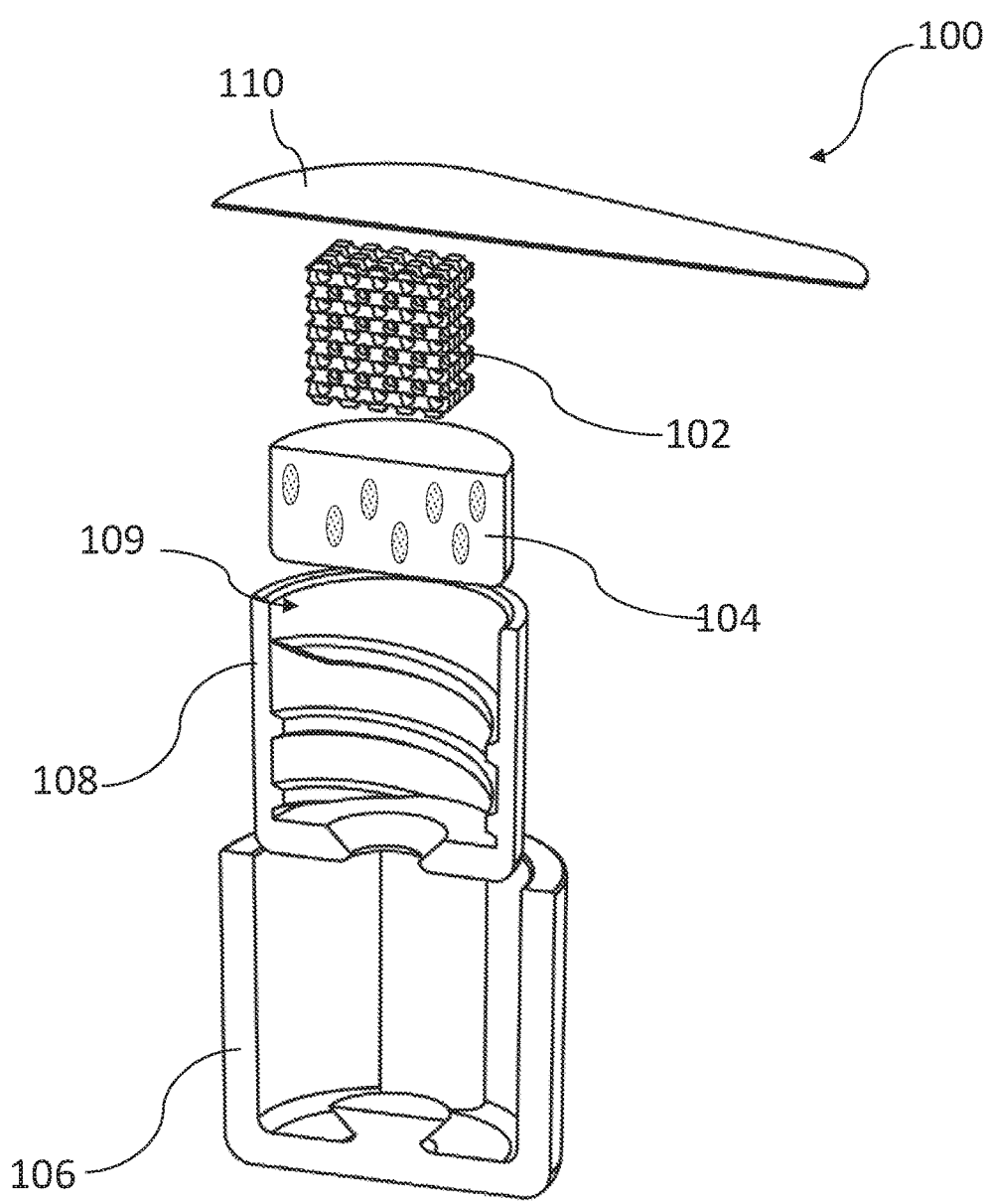
FIG. 3 illustrates an exploded sectional view of the device port cleaner.

Turning to FIGS. 1-3, an embodiment of the device port cleaner 100 is shown. The device port cleaner 100 may comprise an absorbent material 102, a disinfecting agent 104, a container 106, an inner-threaded liner 108 inside the container 106, and a lid 110. Prior to use, the seal or lid 110 may be secured over the container of the device port cleaner 100 to seal and protect the contacting end of the device port cleaner 100 from contamination and other environmental hazards. As shown in FIG. 2, the absorbent material 102 holding the disinfecting agent 104 may be positioned inside the inner-threaded liner 108. The inner-threaded liner 108 may then be inserted into and mated with the container 106. The inner-threaded liner 108, absorbent material 102, and disinfecting agent 104 may then be secured inside the container 106 using the lid 110. The lid 110 may seal the inner components of the device port cleaner 100 inside the container 106. The lid 110 may form a seal directly with the container 106. The lid 110 may be made of various semi-rigid to rigid materials, including plastic, aluminum, polymer, stainless steel, silicone based material, synthetic isoprene, isoprene, and thermoplastics. The lid 110 may be secured over the container 106 using a heat seal method. This listing is illustrative, only, and not intended to be exhaustive. It should be appreciated by one skilled in the art that a wide range of materials or mixtures of materials, with properties similar to the above-listed materials may be used to construct the lid 110.

As shown in FIG. 2, the absorbent material 102 may be secured within the inner-threaded liner 108 such that the absorbent material 102 remains compressible. Compressing the absorbent material 102 may act as a release mechanism for releasing and dispersing the disinfecting agent 104 being held by the absorbent material 102. The absorbent material 102 may be sized and shaped to fit within the inner-threaded liner 108 such that the absorbent material 102 may match the corresponding shape of the inner-threaded liner 108. Alternatively, the absorbent material 102 may be any other shape size as needed to hold the disinfecting agent 104. The absorbent material 102 may be formed from any absorbent, porous, and compressible material including but not limited to a sponge, absorbent cotton, polyurethane, polyvinyl alcohol, silicone, cellulose wood fibers, foam, and foamed plastic polymers. FIG. 2 shows that when the lid 110 is secured to the device port cleaner 100, the absorbent material 102 and the disinfecting agent 104 may be sealed within the container 106 to be protected from contaminants and environmental hazards.

Alternatively, the inner-threaded liner 108 may also contain the disinfecting agent 104 only without the use of the absorbent material 102. The disinfecting agent 104 may be used for cleaning connector ports inserted into the device port cleaner 100. In an embodiment, the disinfecting agent 104 may be any antimicrobial or antiseptic agent including but not limited to isopropyl alcohol, povidine iodine, and the like. The disinfecting agent 104 may also be in a liquid, gel, or hydrogel form with various viscosities. The disinfecting agent 104 may be initially held within the absorbent material 102 and only released when the device port cleaner 100 is used to clean the device port connector.

Figure 4:
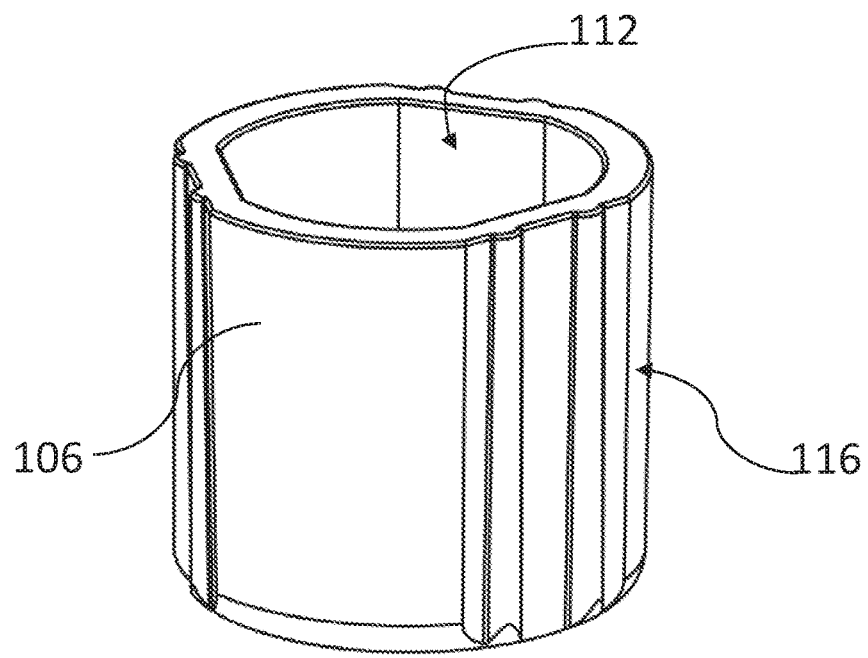
FIG. 4 illustrates a container of the device port cleaner.
Figure 5:
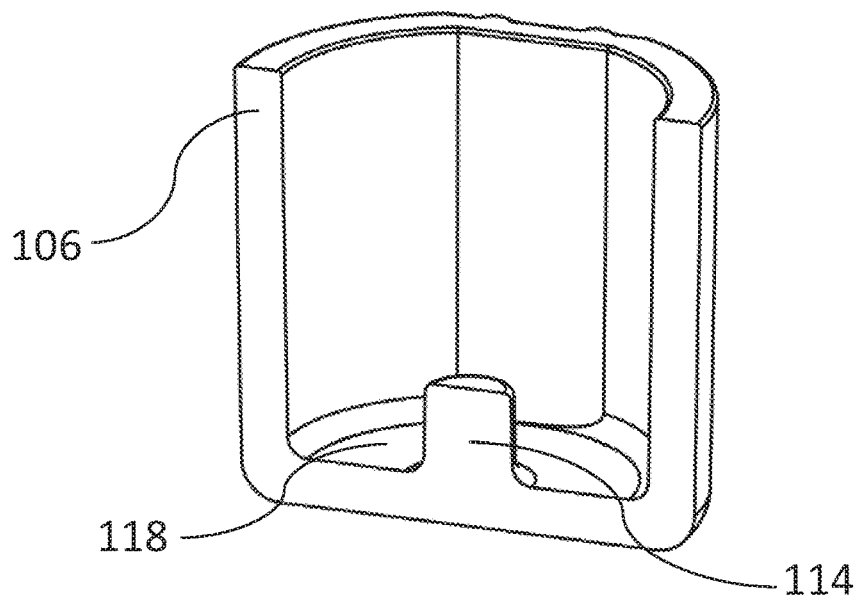
FIG. 5 illustrates a sectional view of the container.

Turning to FIGS. 4 and 5, an embodiment of the container 106 is shown for holding the inner-threaded liner 108 of the device port cleaner 100. The container 106 may comprise a container cavity 112 for holding the inner-threaded liner 108 and a boss 114. The exterior surface of the container 106 may comprise a gripping handle 116 comprising a ribbed surface, grooves, corrugated or channeled elements, and the like to assist the user in manipulating the device port cleaner 100. The gripping handle 116 may man expand around at least a portion of the entire exterior surface of the container 106 to assist the user in handling the device port cleaner 100 in any orientation. The gripping handle 116 may be of various sizes and depth depending on the overall size of the device port cleaner 100. The container 106 may comprise various numbers of gripping handle 116 including 1, 2, 3, 4, etc. The container 106 may also not have a gripping handle 116 at all.

Alternatively, the overall shape of the container 106 may be configured to improve the overall handling of the device port cleaner 100. In the embodiment shown in FIG. 4, the container 106 may be configured to a substantially triangular shape with rounded corners to allow to the device cleaner to be easily manipulated and rotated by the user. The container 106 and overall shape of the cleaner 100 may comprise various other shapes including but not limited to a square with rounded edges, a pentagon with rounded edges, and the like. The inner cavity 112 of the container 106 may be formed to substantially match the outer shape of the container 106. The geometrically shaped inner cavity 112 may prevent the inner-threaded liner 108 from rotating inside the cavity 112 when the inner-threaded liner 108 is affixed inside the container 106. As shown in FIG. 3, the inner cavity 112 of the liner 108 may also comprise a stepped surface 109 to aid in easing the threading of the device port connector 200 into the device port cleaner 100.

The boss 114 may extrude into the inner cavity 112 from an interior base 118 of the container 106. The boss 114 may extrude from a center region of the base 118 of the container 106. The boss 114 may be used for aligning and affixing the inner-threaded liner 108 when the inner threaded liner 108 is mated with the container 106. In the example shown, the boss 114 may be formed in the shape of a cylindrical extrusion. Alternatively, the boss 114 may comprise any other shapes including a cube or prismatic extrusion and the like. When assembling the liner 108 with the container 106, the liner 108 may be aligned over the container 106 such that the boss 114 and the opening 124 in the liner 108 are aligned concentrically. The liner 108 may then be inserted into the container 106 until the boss 114 subsequently is threaded through the opening 124 in the liner 108 and the liner 108 is completely fitted inside the container 106. When assembled, the liner 108 may fit into the container 106 such that the base of the liner 108 may be in contact with the interior surface of base 118 of the container 106.

Figure 6A:
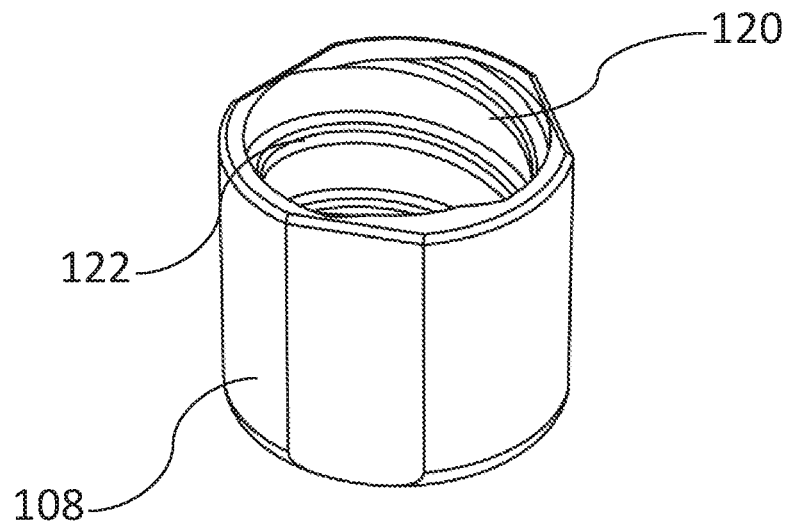
FIGS. 6A and 6B illustrate an isometric and sectional view of an inner-threaded lining of the device port cleaner.
Figure 6B:
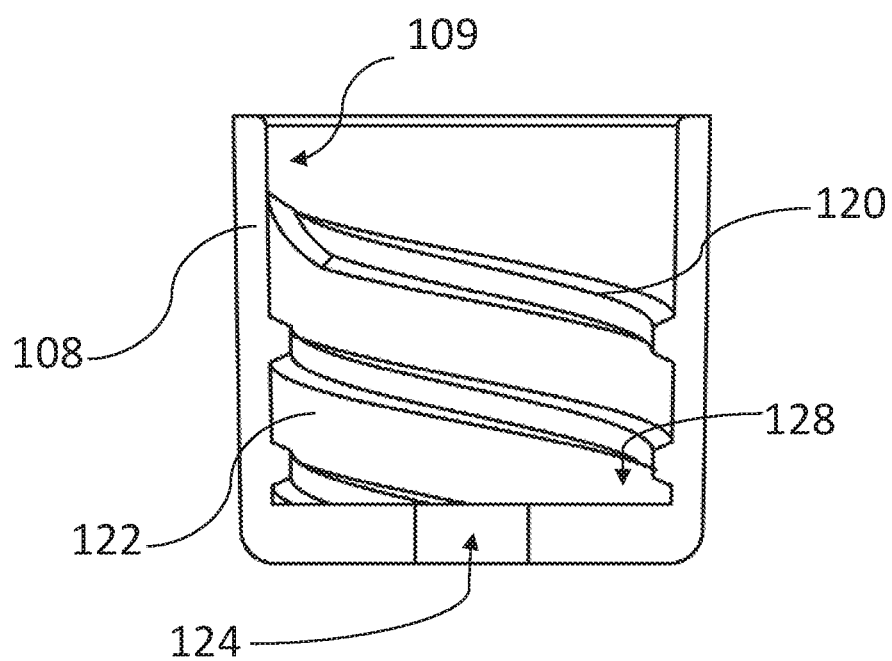

Turning to FIGS. 6A and 6B, an embodiment of the inner-threaded liner 108 is shown. The inner-threaded liner 108 may comprise an outer geometry, the stepped surface 109, and a series of inner threads 120. The outer geometry of the inner-threaded liner 108 may be shaped to substantially match the shape of the inner cavity 112 of the container 106, shown in FIG. 4. Both the inner cavity 112 and the inner-threaded liner 108 may be geometrically shaped to limit rotation or movement of the inner-threaded liner 108 inside the container 106. When the device port connector 200 is threaded into the device port cleaner 100, the fitting between the geometrically shaped container cavity 112 and the inner-threaded liner 108 may prevent rotational movement that may otherwise be caused by the torsional forces from the screwing of the connector into the cleaner 100. When the inner-threaded liner 108 is inserted into the container 106, the exterior surface of the inner-threaded liner 108 may be in direct contact with the interior surface of the container 106.

The inner threads 120 may be formed along an interior surface 122 of the inner-threaded liner 108. The inner thread 120 may allow for a device port connector to be screwed into the device port cleaner 100 during use to access the disinfecting agent 104 inside the device port cleaner 100. The inner thread 120 may assist in enabling a more secure fitting when the device port cleaner 100 is used to clean the device port connector. The inner thread 120 may allow for the device port cleaner 100 to securely retain the connecting end of the device port connector until the device port connector is ready to be used.

The inner thread 120 may comprise a series of teeths formed in the interior surface 122 of the inner-threaded liner 108. Various inner threads 120 may be formed to substantially match with corresponding threading commonly used in device port connectors in the industry. In the embodiment shown in FIG. 6B, the liner 108 may also comprise a stepped surface 109 such that the inner thread 120 may be formed at a distance from the top edge of the inner-threaded liner 108. The stepped surface 109 may be configured to provide some leverage space to initially position the connecting end of the device connector within the cleaner 100. When positioned within the stepped surface 109 of the cleaner 100, the device port connector may then be further manipulated and aligned such that threads of the connector are aligned or matched with the inner threads 120 of the cleaner 100 for threading and insertion. The inner threads 120 of the cleaner 100 may subsequently extend throughout the interior surface 122 of the inner-threaded liner 108 and terminate at the edge of a base 128 of the inner-threaded liner 108. As shown in FIG. 6B, the base 128 of the inner-threaded liner 108 may further comprise an opening 124 for alignment and affixing the inner-threaded liner 108 inside the container 106. The opening 124 may extend throughout the base 128 of the inner-threaded liner 108 creating to allow the boss 114 in the container 106 to extend through.

Figure 7A:
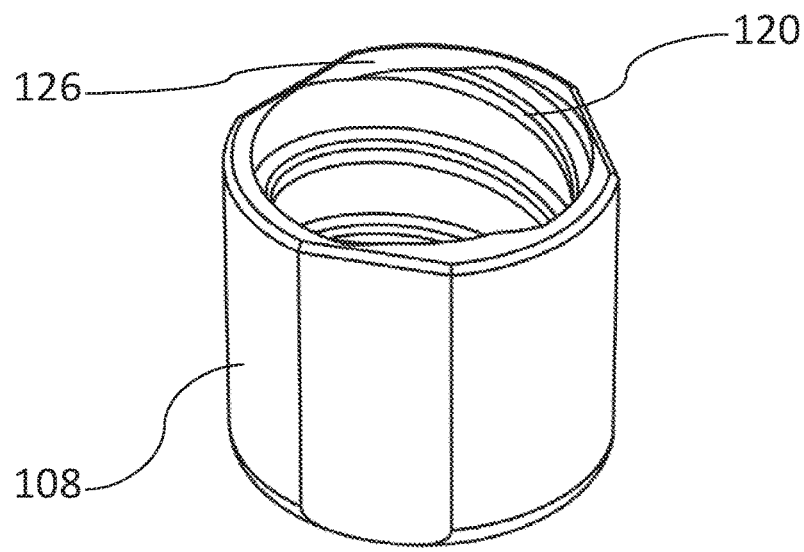
FIGS. 7A and 7B illustrate an isometric and sectional view of another embodiment of the inner-threaded lining.
Figure 7B:
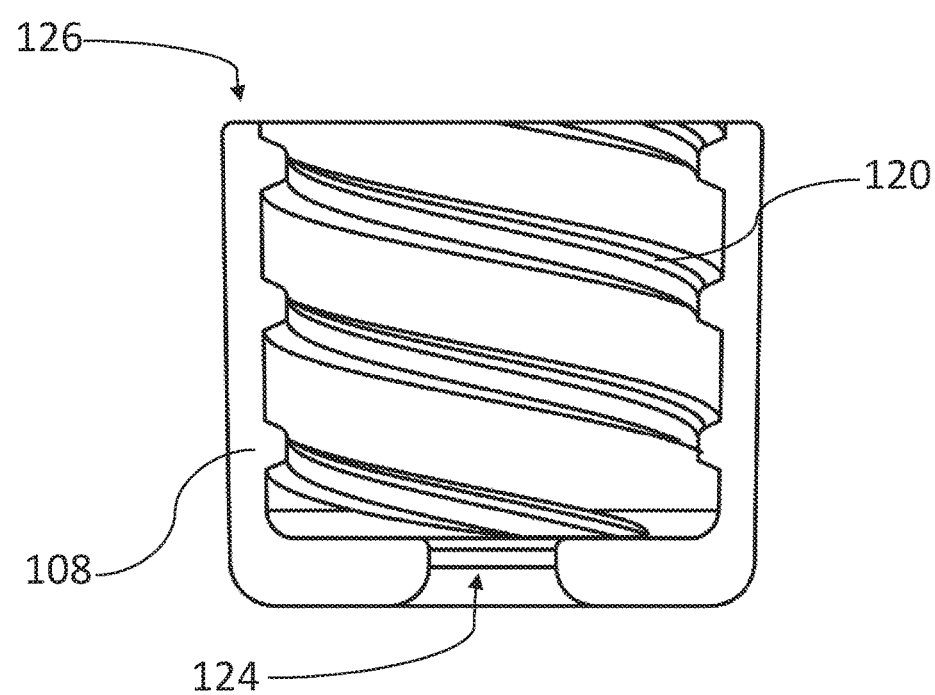

FIGS. 7A and 7B shows another embodiment of the inner-threaded liner 108 without the stepped surface 109. The inner threads 120 may instead start from the top edge 126 of the inner-threaded liner 108 and extend towards the base 118.

Figure 8A:
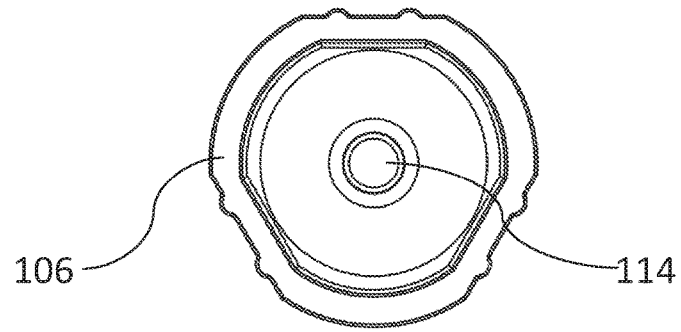
FIGS. 8A-8C illustrate a top view of the container, the inner-threaded liner, and the inner-threaded lining mated with the container, respectively.
Figure 8B:
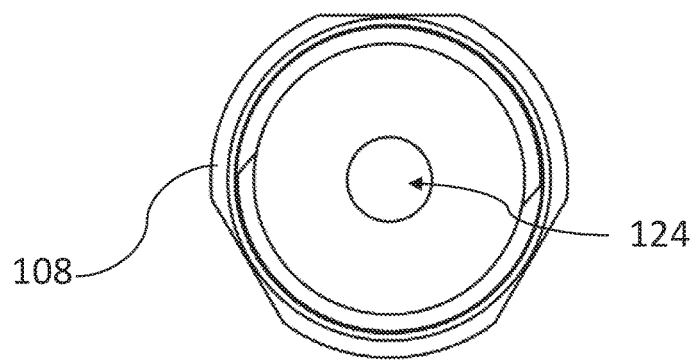
Figure 8C:
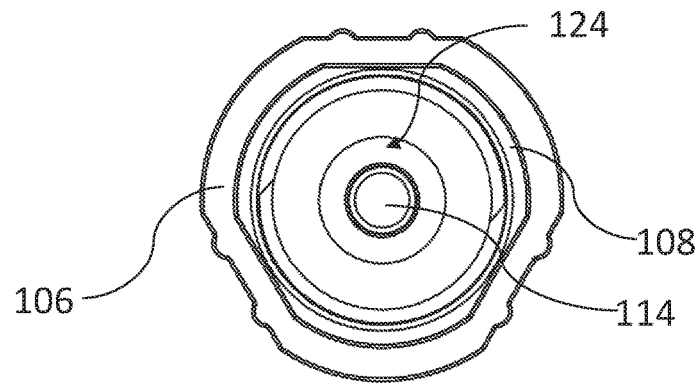

FIGS. 8A-8C show the alignment and fitting of the boss 114 through the opening 124 when the inner-threaded liner 108 is mated with the container 106. The size and shape of the opening 124 may substantially match the size and shape of the boss 114 such that the boss 114 may snuggly fit through the opening 124. The size and shape of the internal geometry of the container cavity 112 may substantially match the size and shape of the external geometry of the inner-threaded lining 208 such that the inner-threaded liner 108 may snuggly fit within the container 106 when mated, as shown in FIG. 8C. In an embodiment, the inner-threaded liner 108 may be bonded or affixed inside the cavity of the container 106 by mechanical means including but not limited to staking, thermal staking, snapfit, radiofrequency welding, ultrasonic welding, laser welding, mechanical fasteners, and the like. Alternatively, the liner 108 may be secured inside the container 106 by an adhesive including but not limited to glue, polyvinyl acetate, aliphatic, cyanoacrylate, epoxy, contest cement, polyurethane glue, and the like. When affixed together, the inner-threaded liner 108 may be permanently retained inside the container 106. The mechanical fastening or bonding of the inner-threaded liner 108 to the container 106 may be at a single point within the container cavity 112 or at multiple points along any surface between the exterior surface of the inner-threaded liner 108 and the interior surface of the container cavity 112. When secured, the bonding element may completely limit the movement of the inner-threaded liner 108 within the container 106.

The separate container 106 and inner-threaded liner 108 of the device port cleaner 100 may allow for the two parts to be manufactured using different materials. The container 106 may be made of various semi-rigid to rigid materials, including but not limited to plastic, polyethylene, aluminum, polymer, stainless steel, silicone based material, synthetic isoprene, isoprene, thermoplastics, and the like. In the preferred embodiment, the container 106 may be a high density polyethylene. The inner-threaded liner 108 may be formed from a soft polymer or plastic including but not limited to thermoplastic vulcanized elastomer (TPV), thermoplastic polyurethane (TPU), silicone, polyether block amide (PEBA), flexible poly vinyl chloride (FPVC) and the like. In the preferred embodiment, the inner-threaded liner 108 may be made of TPV. This listing is illustrative, only, and not intended to be exhaustive. It should be appreciated by one skilled in the art that a wide range of materials or mixtures of materials, with properties similar to the above-listed materials may be used to construct the device port cleaner 100.

In alternative embodiments, the two components of the device port cleaner 100 may be constructed of the same material. The device port cleaner 100 may also be provided with additional, fewer, or different components that those of the embodiment shown. As an example, the container 106 and the inner-threaded liner 108 may be constructed as a single unitary component.

Figure 9:
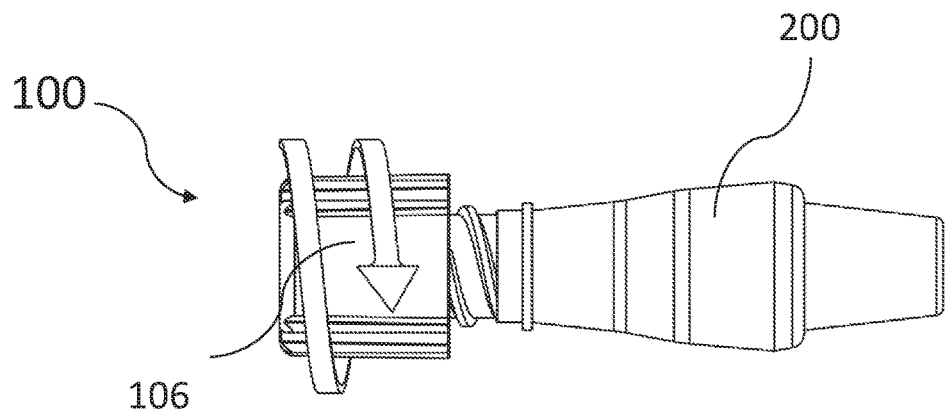
FIG. 9 illustrates a device port connector threaded into the device port cleaner.
Figure 10:
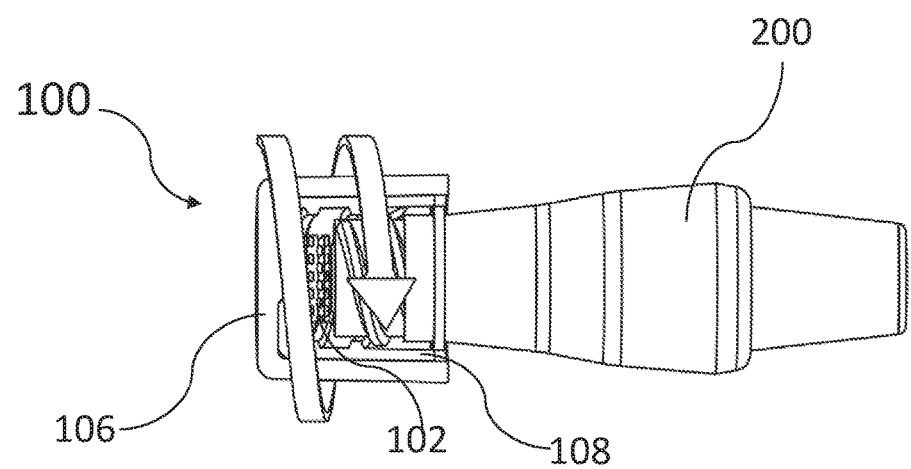
FIG. 10 illustrates a sectional view of the device port cleaner as the device port connector is threaded.

Once the device port cleaner 100 is assembled, FIGS. 9 and 10 show a device port connector 200 being threaded into the device port cleaner 100 for cleaning. As shown in FIG. 9, the device port connector 200 may comprise standard threading along the outer surface of the contacting end. The standard threading may mate with the inner thread 120 inside the inner-threaded liner 108 to secure the device port connector 200 to the device port cleaner 100 for cleaning. The inner thread 120 of the inner-threaded liner 108 may further comprise a flexible soft polymer material such that the inner threads 120 may conform to the geometry of the standard threading on the device port connector 200 to further ease the threading of the device port connector 200 the device port cleaner 100 together. The soft polymer material used for the liner 108 may also withstand treatment and not degrade during the sterilization process during manufacturing. The threading movement to secure the cleaner 100 to the device port connector 200 for cleaning may disperse the disinfecting agent 104 and act as scrub to clean the exterior surface of the connector 200. In addition to the embodiment shown, the inner threadings 120 within the inner-threaded liner 108 may be formed with various shapes, sizes, and designs to complement various device port connectors that the device port cleaner 100 may be used with.

When the device port connector 200 is threaded into the device port cleaner 100, the device port connector 200 may contact and compress the absorbent material 102 inside the inner-threaded liner 108, as shown in FIG. 10. The compression of the absorbent material 102 may act as a release mechanism for the disinfecting agent 104 dispersing and exposing the device port connector 200 to the disinfecting agent 104 as the connector 200 is inserted into the cleaner 100. The interior of the inner-threaded liner 108 may therefore be sized to substantially fit the device port connector 200, the compressed absorbent material 102, and the released disinfecting agent 104. When the device port connector 200 is completely threaded into and secured to the device port cleaner 100, a hermetic seal may be formed between the components of the device port cleaner 100 and the inserted device port connector 200.

Figure 11:
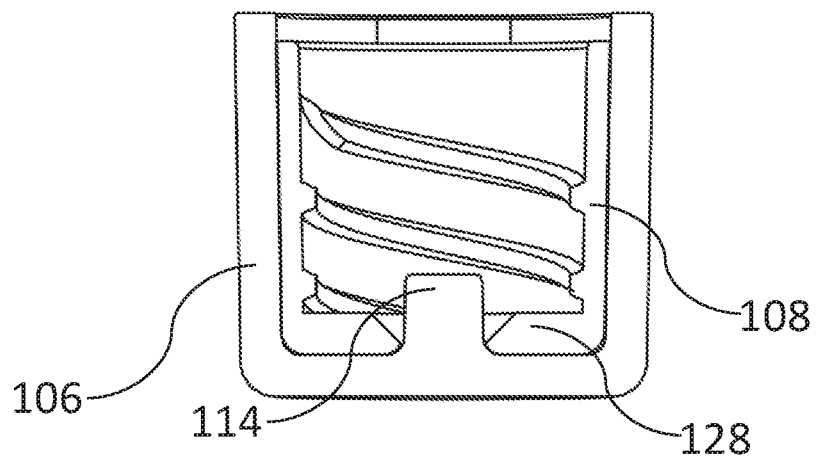
FIG. 11 illustrates a sectional view of an embodiment of the container with an unstaked boss fitted through an opening in the inner-threaded lining.
Figure 12:
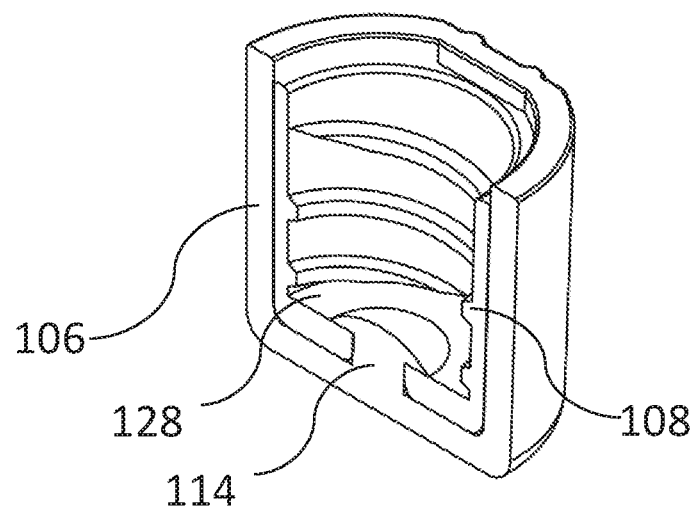
FIG. 12 illustrates a sectional view of another embodiment of the container with a staked boss securing the inner-threaded lining.

Turning to FIGS. 11 and 12, after the internal-threaded liner 108 is aligned with the container 106 and the boss 114 is inserted through the opening 124, the boss 114 extending through the base 128 of the inner-threaded liner 108 may initially be unstaked as in FIG. 11. In the embodiment shown in FIG. 12, to secure the inner-threaded liner 108 to the container 106, the unstaked boss 114 may be staked to mechanically affix the inner-threaded liner 108 and the container 106 together without the need for additional materials such as an adhesive agent, additional screw, or the like. The boss 114 may be staked using a thermal staking or staking punch process to expand the boss 114 radially and compress it axially so as to form an interference fit with the base 128 of inner-threaded liner 108. The staked boss may prevent migration and axial displacement of the inner-threaded liner 108 once inserted into the container 106. To allow for staking of the boss 114, the boss 114 may be sized such that when fitted with the inner-threaded liner 108, the boss 114 may extend just above the base 128 of the inner-threaded liner 108 as shown in FIG. 11. The staked boss 114 may function as a rivet in forming a permanent joint to secure the inner-threaded liner 108 to the container 106 when the device port cleaner 100 is assembled. The thermal staking of the boss 114 may include but is not limited to thermal tooling, thermal punch, hot punch, hot air cold upset, ultrasonic staking, cold forming, infrared staking, and the like.

Figure 13A:
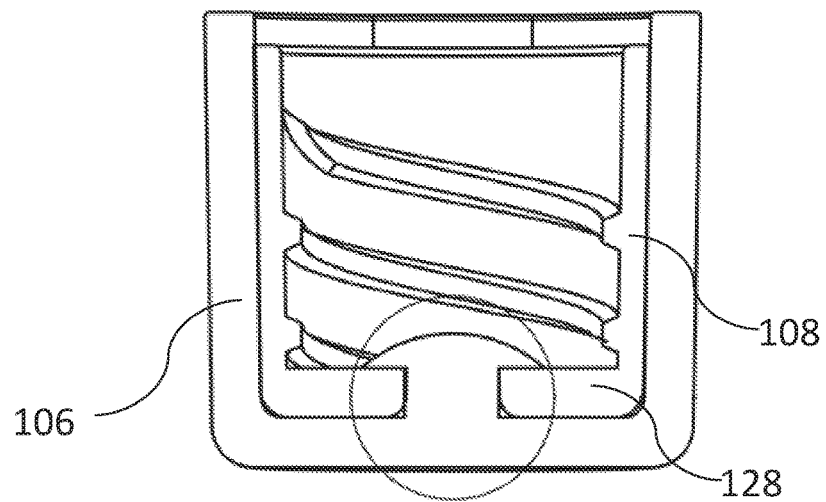
FIGS. 13A and 13B illustrate a sectional view of the container with a dome stake mated to the inner-threaded lining and a close-up of the profile of the dome stake, respectively.
Figure 13B:
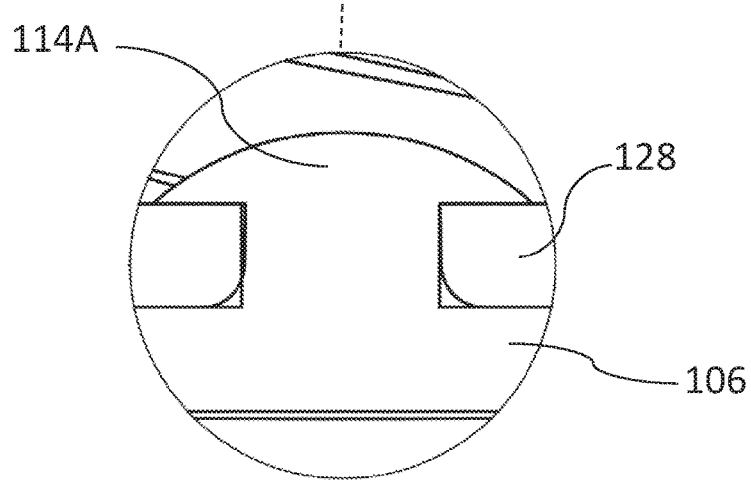

FIGS. 13A-16B show various embodiments of the staked boss 114. In FIGS. 13A and 13B, the inner-threaded liner 108 may be secured by a dome stake 114A. As shown in FIG. 13B, the staked portion of the boss 114 forms a dome over the opening 124 creating an interference fit with the base 128 of the inner-threaded liner 108 of the cleaner 100.

Figure 14A:
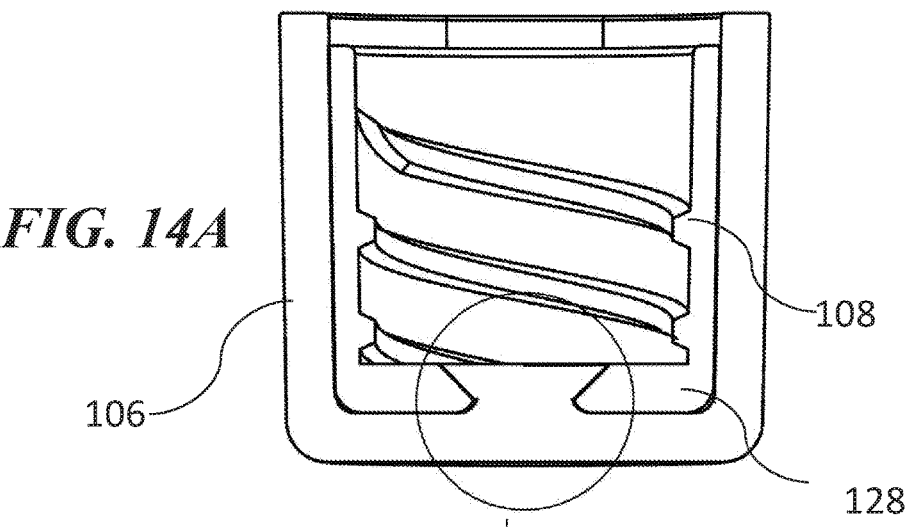
FIGS. 14A and 14B illustrate a sectional view of the container with a flushed stake mated to the inner-threaded lining and a close-up of the profile of the flushed stake, respectively.
Figure 14B:
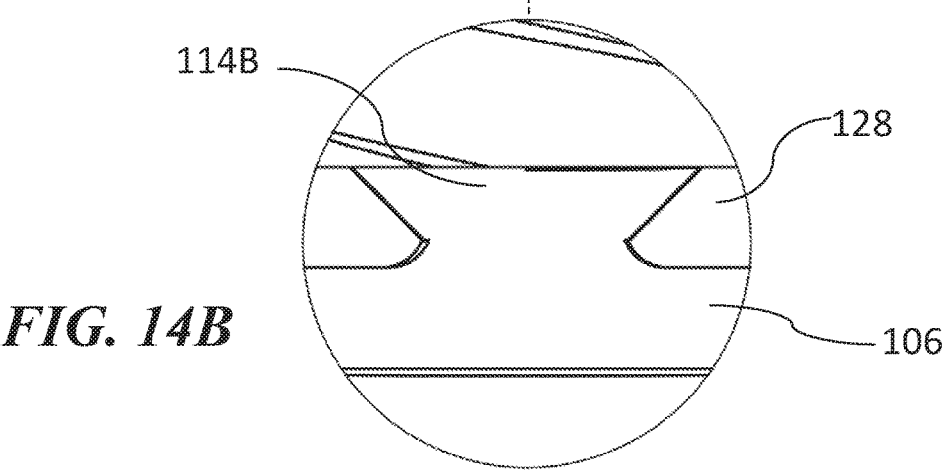

In FIGS. 14A and 14B, the inner-threaded liner 108 may be secured by a flushed stake 114B. As shown in FIG. 14B, the opening 124 in the base 128 of the inner-threaded liner 108 may be formed with a tapered circumference such that when the extruding boss 114 is staked, the expanding portion of the boss 114 fills the tapered circumference of the opening 124 and the top surface of the staked boss 114B is flush with the inner surface of the base 128 of the inner-threaded liner 108. The flushed stake 114B may then create an interference fit with the tapered portion of the base 128 to secure the inner-threaded liner 108 to the container 106.

Figure 15A:
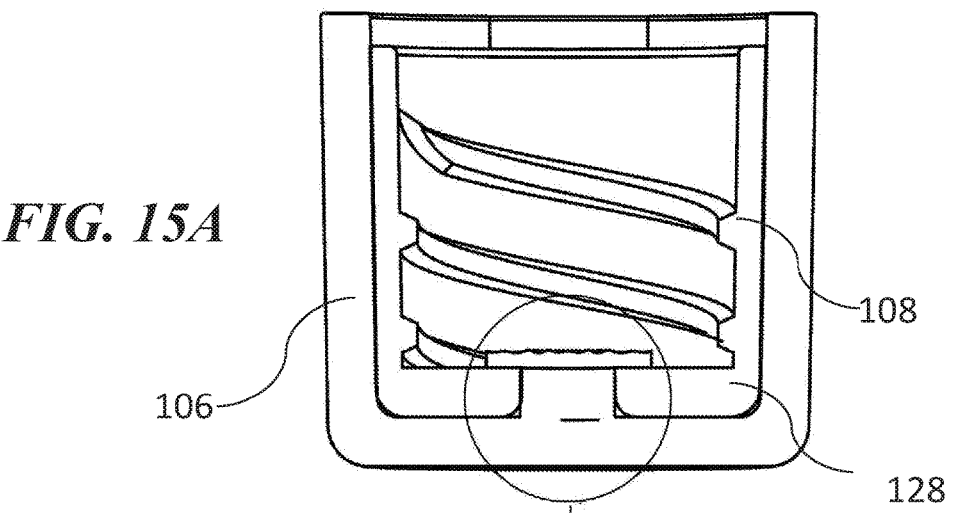
FIGS. 15A and 15B illustrate a sectional view of the container with a knurled stake mated to the inner-threaded lining and a close-up of the profile of the knurled stake, respectively.
Figure 15B:
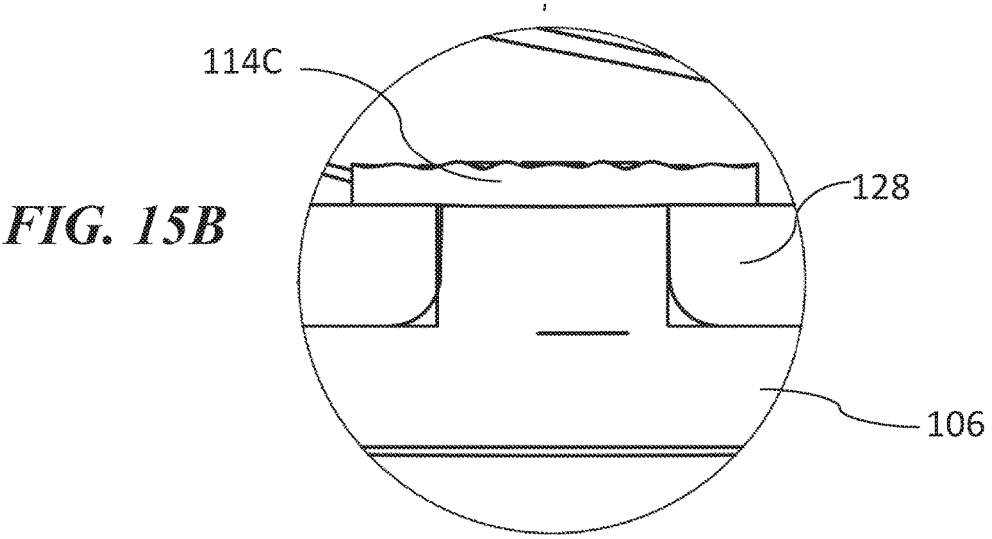

In FIGS. 15A and 15B, the inner-threaded liner 108 may be secured by a knurled stake 114C. As shown in FIG. 15B, the staked portion of the boss 114 may form a knurled stake over the opening 124 creating an interference fit with the base 128 of the inner-threaded liner 108 of the cleaner 100.

Figure 16A:
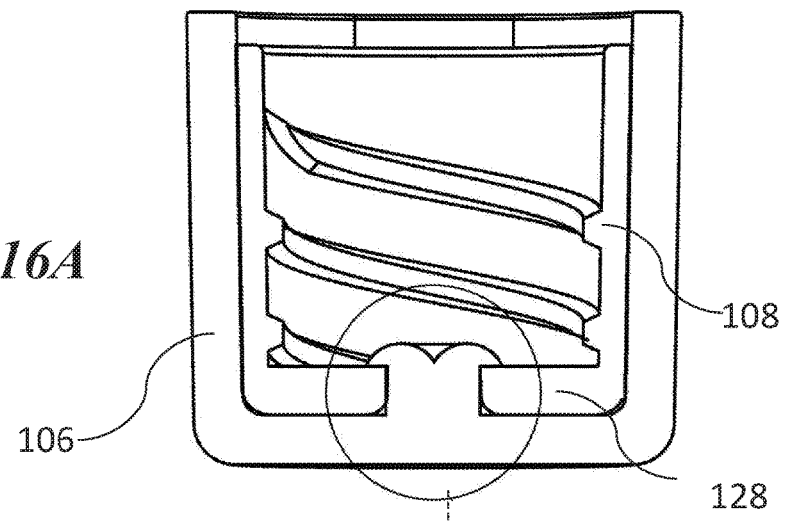
FIGS. 16A and 16B illustrate a sectional view of the container with a rosette stake mated to the inner-threaded lining and a close-up of the profile of the rosette stake, respectively.
Figure 16B:
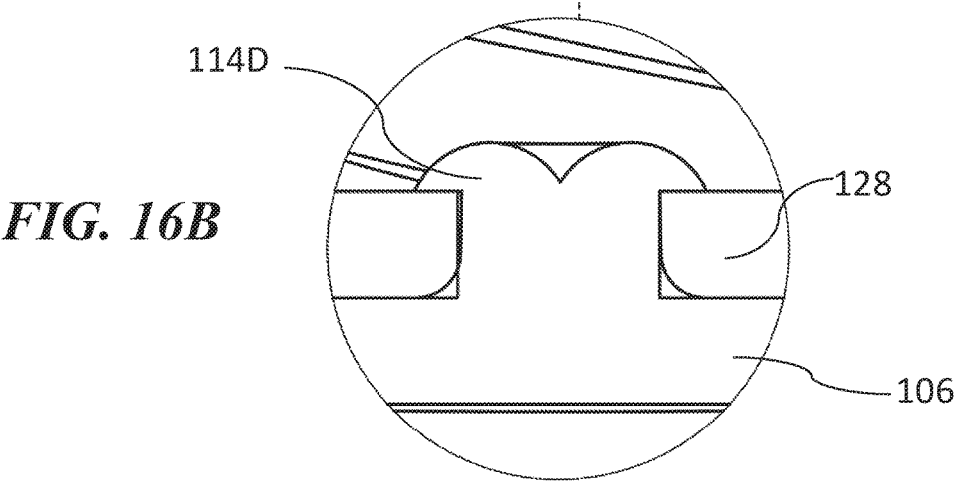

FIGS. 16A and 16B show yet another embodiment of the staked boss 114. The inner-threaded liner 108 may also be secured by a rosette stake 114D. As shown in FIG. 16B, the staked portion of the boss 114 may form a rosette stake over the opening 124 creating an interference fit with the base 128 of the inner-threaded liner 108 of the cleaner 100.

Figure 17:
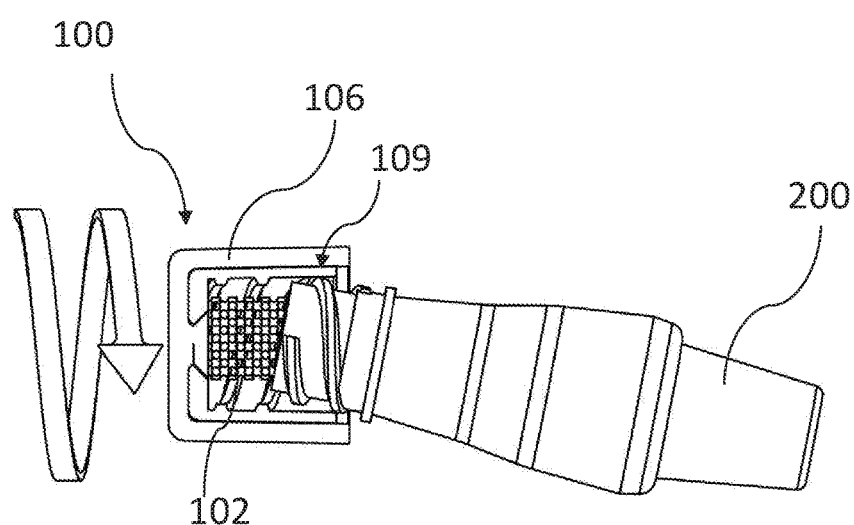
FIG. 17 illustrates a sectional view of a stepped entrance as the device port connector is threaded into the device port cleaner.

Turning to FIG. 17, the device port connector 200 is shown being threaded into an embodiment of the device port cleaner 100 with a stepped surface 109. The stepped surface 109 may assist the user in securing the device port cleaner 100 to the device port connector 200 by correcting misalignments between the device port connector 200 and the device port cleaner 100 prior to the device port connector 200 engaging the cleaner threads 120.

Figure 18:
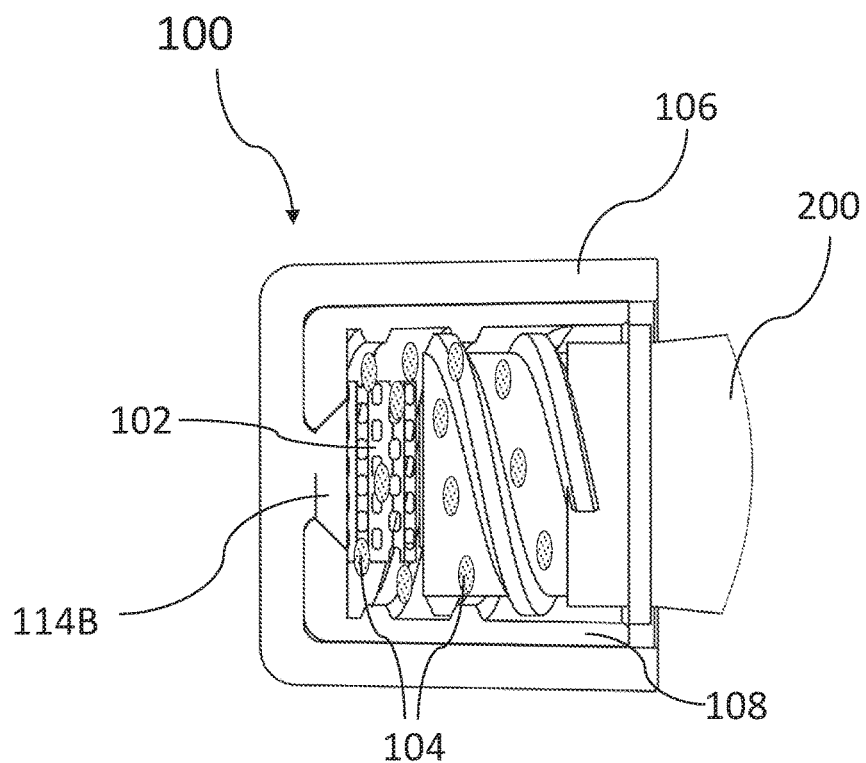
FIG. 18 illustrates a sectional view of the device port connector exposed to a disinfecting solution as the device port connector is threaded into the device port cleaner.

FIG. 18 shows the disinfecting agent 104 released into the inner-threaded liner 108 by the simultaneous compression of the absorbent material 102 with the insertion of the device port connector into the receptacle 108 by, in this example, threading of the device port connector 200 into the device port cleaner 100. The amount of disinfecting agent 104 held by the absorbent material 102 may be a predetermined amount capable of dispersing over some or preferably the entire surface of the portion of the device port connector 200 intended to be inserted into the device port cleaner 100.

The absorbent material 102 may be sized such that the absorbent material 102 fits snuggly inside the inner liner 108. The size of the absorbent material 102 may be large enough such that when contacted by the connector 200 being threaded into the cleaner 100, the connector compresses the absorbent material 102 against the base of the liner 108. The absorbent material 102 may be sized such that the absorbent material 102 would not itself be threaded into the opening in the connector 200 when the connector 200 is being connected. The size and compressibility of the absorbent material 102 may ensure that the connector 200 compresses the absorbent material 102 thereby releasing the disinfecting agent 104 when threaded into the cleaner 100.

Figure 19:
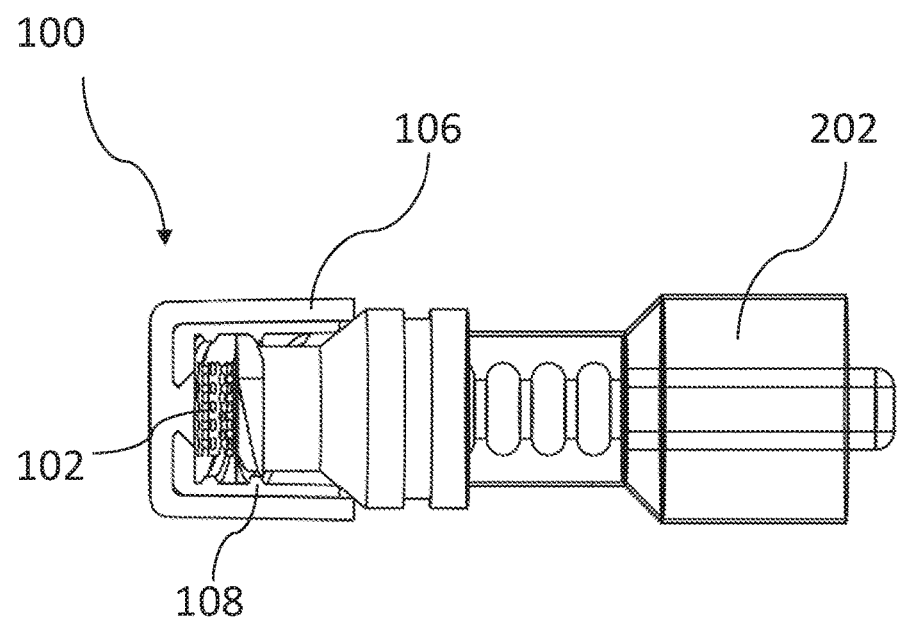
FIG. 19 illustrates the device port cleaner being used to clean a smartsite device port connector.
Figure 20:
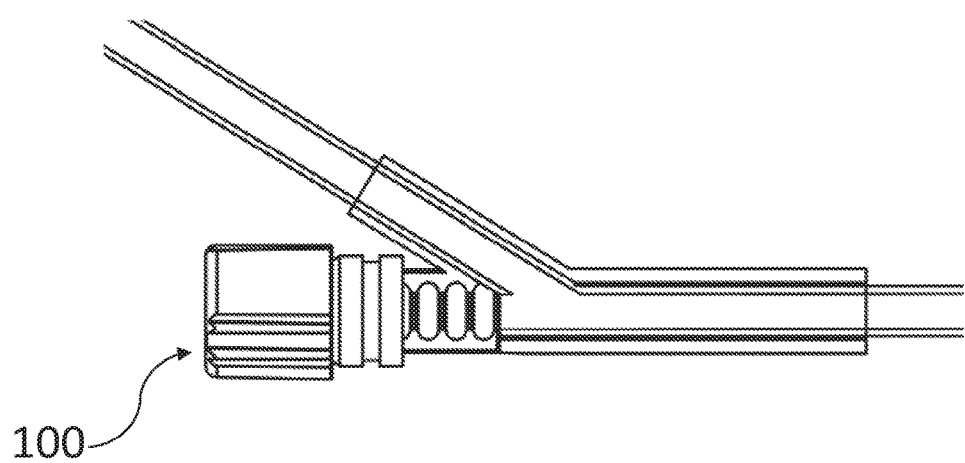
FIG. 20 illustrates the device port cleaner being used to clean a device port connector with a Y-adapter.

FIGS. 19 and 20 show various device port connectors the device port cleaner 100 may be used with. An embodiment of the device port cleaner 100 is shown being used with a smartsite device port connector in FIG. 19. Alternatively, the device port cleaner 100 may be used with a device port connector 200 having a Y-type adapter as shown in FIG. 20.

Figure 21:
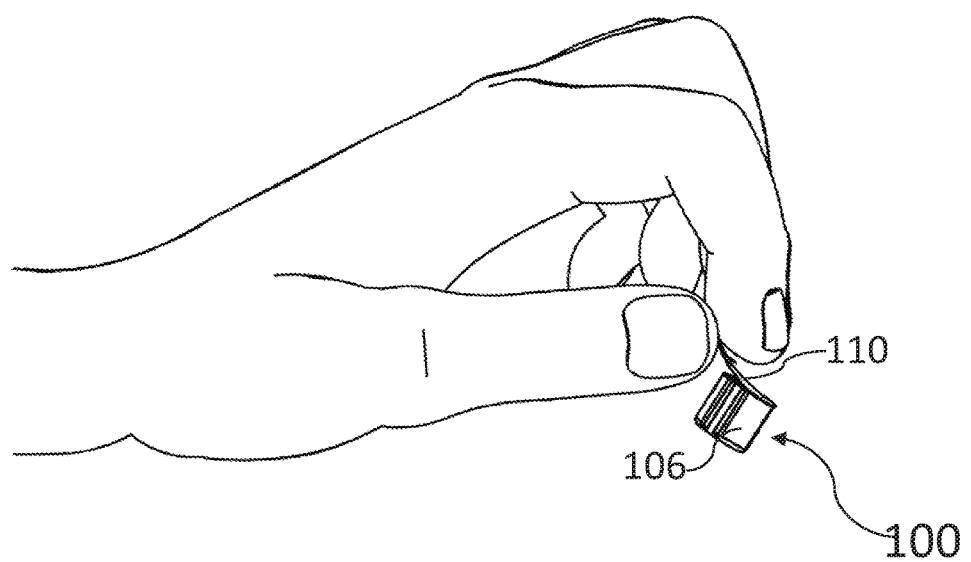
FIG. 21 illustrates a user preparing to use an embodiment of the device port cleaner.

FIG. 21 shows a user preparing the device port cleaner 100 for use. Prior to using the device port cleaner 100, the user may first remove the lid 110 from the container 106 to expose the opening in the inner-threaded liner 108. After the lid 110 is removed, the device connector 200 may then be threaded into the device port cleaner 100 for cleaning.

Figure 22:
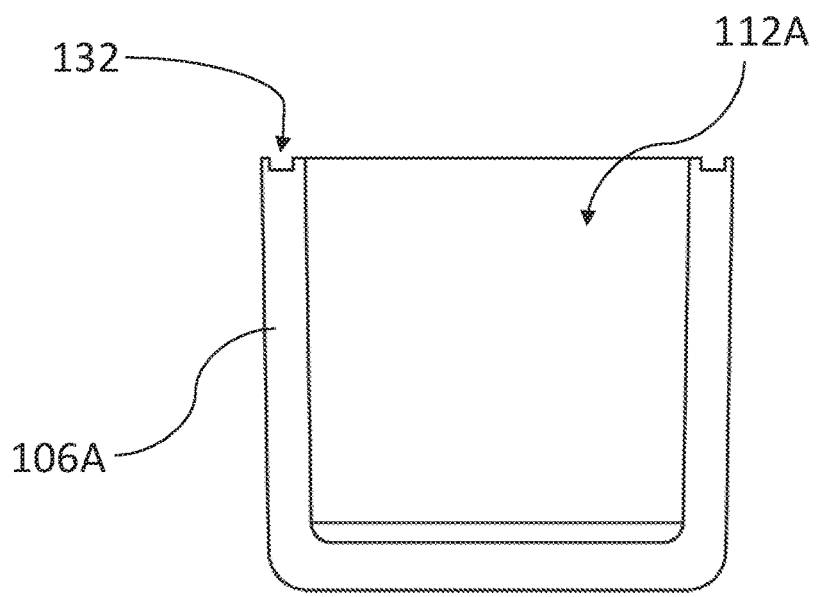
FIGS. 22-24 illustrate yet another embodiment of the device port cleaner designed to be assembled using a spin welding process.
Figure 23:
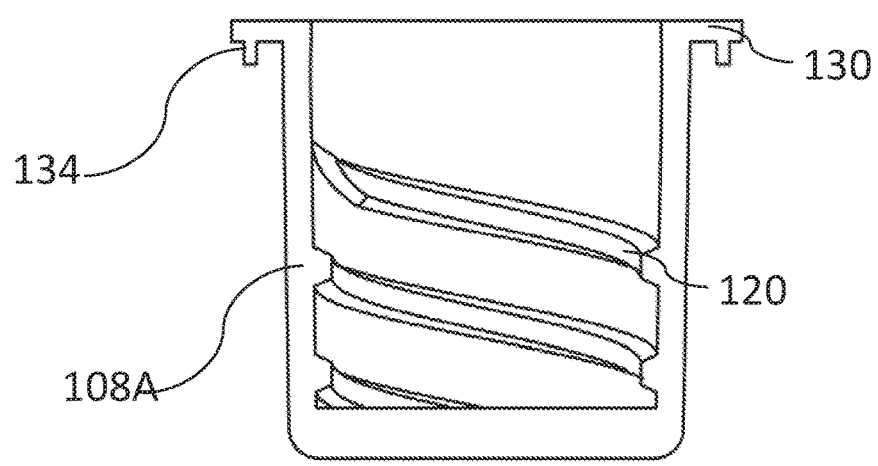
Figure 24:
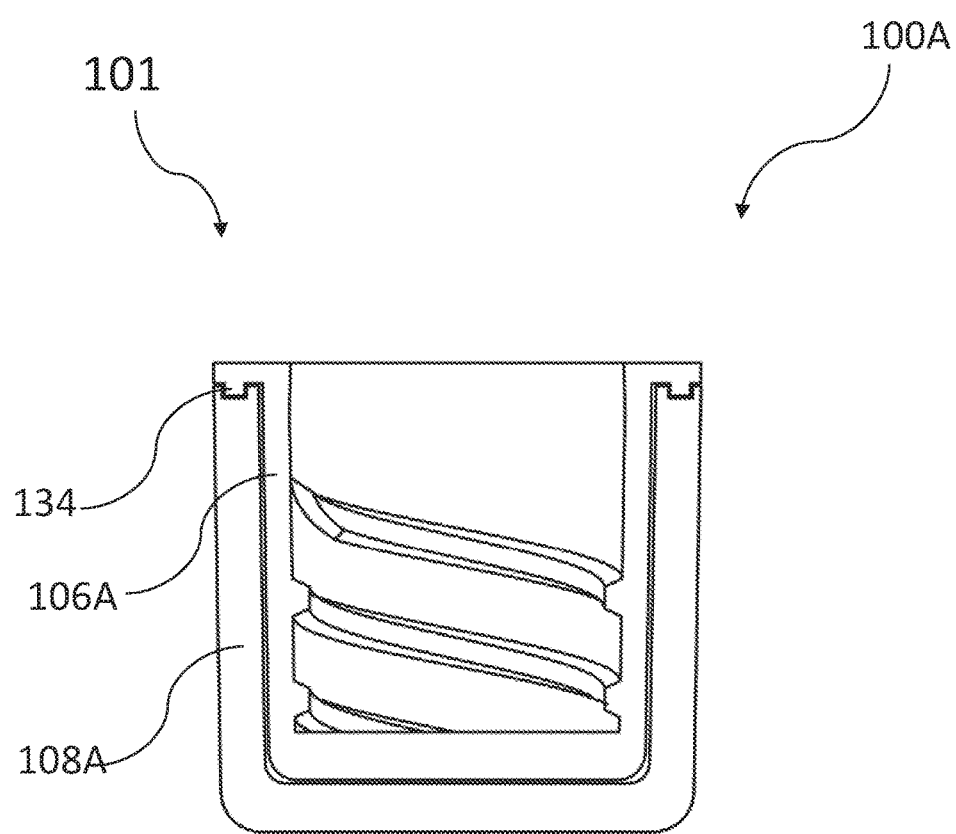

FIGS. 22-24 show an embodiment of the device port cleaner 100A where the inner-threaded liner 108A may be affixed to the container 106A using a friction welding process including but not limited to spin welding. In the embodiment shown, the interior cavity 112A of the container 106A may be a cylindrical cut out such that the inner-threaded liner 108A may rotate within the container 106 when inserted. The external geometry of the inner-threaded liner 108A may similarly be cylindrical to substantially match the shape of the cavity 112A to allow for rotation. As shown in FIG. 22, the container 106A may be formed with a one or more grooves 132 extending along the circumference of the top edge of the container 106A, continuously or intermittently. The groove 132 may be formed to receive a portion of the inner-threaded liner 108A to be used to weld the container 106A and liner 108A together.

To allow for the spin welding of the inner-threaded liner 108A with the container 106A, as shown in FIG. 23, the top edge of the inner-threaded liner 108A may further comprise a flange 130 extruding outwards from the circumference of the top edge of the liner 108A. The flange 130 may further comprise one or more welding members 134 extending downwards from the bottom surface of the flange 130. The one or more welding members 134 extending from the flange 130 may encircle the entire body of the liner 108A, continuously or intermittently. The one or more welding members 134 may be formed to align and fit within the one or more grooves 132 in the container 106A when the inner-threaded liner 108A is inserted into the container 106A. The one or more welding members 134 may be positioned and sized to snuggly fit within the one or more grooves 132 when the inner-threaded liner 108A is assembled within the container 106A. FIG. 24 shows the device port cleaner 100A assembled by spin welding the inner-threaded lining 108A to the container 106A. The mating of the one or more welding members 134 within the one or more grooves 132 may secure the inner-threaded lining 106A and the container 108A together. In addition to spin welding, other variations of friction welding known to one of ordinary skill in the art may be used including but not limited to linear welding, orbital welding, angular welding, and the like.

Having thus described the present invention by reference to certain of its exemplary embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of exemplary embodiments. Accordingly, it is appropriate that any claims supported by this description be construed broadly and in a manner consistent with the scope of the invention.

The invention claimed is:

1. A port cleaner for cleaning a port connector, comprising:
a housing container comprising a housing cavity extending from a housing base to a housing opening;
a boss extending from the housing container into the housing cavity;
an interior container affixed within the housing container wherein the interior container comprises an internal cavity extending from a proximal end to a distal end, wherein the proximal end comprises a container opening configured for receiving a port connector, and wherein the container opening is aligned concentrically within the housing opening;
wherein the interior container comprises an interior opening configured to receive the boss into the internal cavity when the interior container is inserted into the housing cavity;
wherein the interior container is secured within the housing container by staking the boss extending into the internal reservoir to form an interference fit with the interior container; and
a compressible member disposed within the interior container and configured to release a disinfecting agent into the internal cavity.

2. The port cleaner in claim 1, wherein:
the boss extends from the housing base towards the housing opening;
the interior opening is at the distal end of the interior container; and
wherein the interior container is affixed within the housing container by staking the boss extending through the interior opening at the distal end of the interior container to form an interference fit with the interior container.

3. The port cleaner in claim 1, further comprising a cleaner lid configured to seal the interior container and compressible member inside the housing cavity.

4. The port cleaner in claim 1, wherein the interior container is secured within the housing container by a mechanical fastener.

5. The port cleaner in claim 1, wherein the interior container is secured within housing container by an adhesive.

6. The port cleaner in claim 1, wherein the interior container further comprises a series of threads at the container opening configured for threading a port connector.

7. The port cleaner in claim 6, wherein the interior container further comprises a stepped surface between the threads and the container opening.

8. The port cleaner in claim 1, wherein the compressible member further comprises an absorbent material.

9. The port cleaner in claim 8, wherein the compressible member is configured to release the disinfecting agent when the absorbent material is compressed.

10. The port cleaner in claim 1, wherein the compressible member is configured to release the disinfecting agent into the internal cavity when the port cleaner is used.

11. The port cleaner in claim 1, wherein the housing cavity comprises a geometrical cutout and the interior container comprises an external geometrical shape substantially matching the geometrical cutout of the housing cavity, wherein when the interior container is inserted in the housing cavity, the fitting of the interior container within the housing cavity prevents rotation of the interior container within the housing cavity.

12. The port cleaner in claim 1, wherein an outer surface of the housing container further comprises a gripping handle.

13. The port cleaner in claim 1, wherein the disinfecting agent comprises isopropyl alcohol.

14. The port cleaner in claim 2, wherein the interior container is affixed within the housing container by a dome stake.

15. The port cleaner in claim 2, wherein the interior container is affixed within the housing container by a flush stake.

16. The port cleaner in claim 2, wherein the interior container is affixed within the housing container by a knurled stake.

17. The port cleaner in claim 2, wherein the interior container is affixed within the housing container by a rosette stake.

18. A port cleaner for cleaning a port connector, comprising:
a housing container comprising a housing cavity extending from a housing base to a housing opening, wherein the housing container further comprises a boss extending from the housing base towards the housing opening;
an interior container affixed within the housing container wherein the interior container comprises an internal cavity extending from a proximal end to a distal end, wherein the proximal end comprises a container opening configured for receiving a port connector, and wherein the container opening is aligned concentrically within the housing opening;

wherein the distal end comprises an interior opening at the distal end configured to receive the boss into the internal cavity when the interior container is inserted into the housing cavity of the housing container;

wherein the interior container is affixed within the housing container by staking the boss extending through the interior opening to form an interference fit with the interior container;

a compressible member disposed within the interior container and configured to release a disinfecting agent into the internal cavity; and a cleaner lid configured to seal the interior container and compressible member inside the housing cavity.

19. The port cleaner in claim 18, wherein the interior container is secured within housing container by an adhesive.

20. The port cleaner in claim 18, wherein the interior container further comprises a series of threads at the container opening configured for threading a port connector.

21. The port cleaner in claim 20, wherein the interior container further comprises a stepped surface between the threads and the container opening.

22. The port cleaner in claim 18, wherein the compressible member comprises an absorbent material.

23. The port cleaner in claim 22, wherein the compressible member is configured to release the disinfecting agent when the absorbent material is compressed.

24. The port cleaner in claim 18, wherein the housing cavity comprises a geometrical cutout and the interior container comprises an external geometrical shape substantially matching the geometrical cutout of the housing cavity, wherein when the interior container is inserted in the housing cavity, the fitting of the interior container within the housing cavity prevents rotation of the interior container within the housing cavity.

25. The port cleaner in claim 18, wherein an outer surface of the housing container further comprises a gripping handle.

26. The port cleaner in claim 18, wherein the disinfecting agent comprises isopropyl alcohol.

27. The port cleaner in claim 18, wherein the interior container is affixed within the housing container by a dome stake.

28. The port cleaner in claim 18, wherein the interior container is affixed within the housing container by a flush stake.

29. The port cleaner in claim 18, wherein the interior container is affixed within the housing container by a knurled stake.

30. The port cleaner in claim 18, wherein the interior container is affixed within the housing container by a rosette stake.

31. The port cleaner in claim 1, wherein the interior container comprises a soft polymer, soft plastic, thermoplastic vulcanized elastomer (TPV), thermoplastic polyurethane (TPU), silicone, polyether block amide (PEBA), or flexible poly vinyl chloride (FPVC).

32. The port cleaner in claim 18, wherein the interior container comprises a soft polymer, soft plastic, thermoplastic vulcanized elastomer (TPV), thermoplastic polyurethane (TPU), silicone, polyether block amide (PEBA), or flexible poly vinyl chloride (FPVC).

* * * * *